United States Patent
Huang et al.

(10) Patent No.: US 11,213,277 B2
(45) Date of Patent: Jan. 4, 2022

(54) MEASURING APPARATUS AND SYSTEM FOR MEASURING ELASTICITY OF BIOLOGICAL TISSUE

(71) Applicant: National Cheng Kung University, Tainan (TW)

(72) Inventors: Chih-Chung Huang, Tainan (TW); Pei-Yu Chen, New Taipei (TW); Cho-Chiang Shih, New Taipei (TW)

(73) Assignee: National Cheng Kung University, Tainan (TW)

( * ) Notice: Subject to any disclaimer, the term of this patent is extended or adjusted under 35 U.S.C. 154(b) by 65 days.

(21) Appl. No.: 16/706,913

(22) Filed: Dec. 9, 2019

(65) Prior Publication Data
US 2021/0169452 A1    Jun. 10, 2021

(51) Int. Cl.
*A61B 8/08*    (2006.01)
*A61B 8/00*    (2006.01)

(52) U.S. Cl.
CPC ............ *A61B 8/485* (2013.01); *A61B 8/4427* (2013.01); *A61B 8/461* (2013.01); *A61B 8/54* (2013.01); *A61B 8/56* (2013.01)

(58) Field of Classification Search
CPC ........... A61B 8/485; A61B 8/54; A61B 8/461; A61B 8/4427; A61B 8/56; A61B 8/5223
See application file for complete search history.

(56) References Cited

U.S. PATENT DOCUMENTS

| | | | |
|---|---|---|---|
| 2011/0055447 A1* | 3/2011 | Costa | A61B 8/4433 710/304 |
| 2018/0014811 A1* | 1/2018 | Sonnenschein | A61B 8/4472 |
| 2020/0029934 A1* | 1/2020 | Sandrin | A61B 8/429 |
| 2020/0054217 A1* | 2/2020 | Parker | A61B 5/7239 |
| 2020/0390421 A1* | 12/2020 | Audi Re | A61B 8/485 |

FOREIGN PATENT DOCUMENTS

| KR | 20200041550 | * 4/2020 | ........... A61B 5/7275 |
|---|---|---|---|

OTHER PUBLICATIONS

Sandrin, Laurent & Oudry, Jennifer & Bastard, Cécile & Celine, Fournier & Miette, Veronique & Mueller, Sebastian, "Non-Invasive Assessment of Liver Fibrosis by Vibration-Controlled Transient Elastography (Fibroscan)" Sep. 2011, "Liver Biopsy" Chapter 19. (Year: 2011).*

\* cited by examiner

*Primary Examiner* — Amanda Lauritzen Moher
(74) *Attorney, Agent, or Firm* — Banner & Witcoff, Ltd.

(57) ABSTRACT

A measuring system for measuring elasticity of biological tissue includes a mobile device and a measuring apparatus including a conducting seat and a measuring device. The conducting seat is for detachable mounting of the mobile device therein, and is adapted to abut against the biological tissue for conducting vibrations produced by the mobile device to the biological tissue to cause the biological tissue to vibrate. The measuring device includes an ultrasonic transducer to emit an ultrasound signal to the biological tissue and an elasticity analyzer to analyze an ultrasound echo signal that results from reflection of the ultrasound signal by the biological tissue which is vibrating to obtain an elasticity data of the biological tissue.

12 Claims, 4 Drawing Sheets

MEASURING APPARATUS AND SYSTEM FOR MEASURING ELASTICITY OF BIOLOGICAL TISSUE

FIELD

The disclosure relates to a measuring apparatus and system, more particularly to a measuring apparatus and system for measuring elasticity of a biological tissue.

BACKGROUND

A conventional ultrasonic measuring system for measuring an elasticity of an object is commonly used in clinical trials or industrial inspection. The conventional ultrasonic measuring system usually analyzes and converts elastic waves propagating in the object under test to an elasticity information such as Young's modulus to obtain the elasticity of the object. To measure an elasticity of a soft tissue, the conventional ultrasonic measuring system utilizes an external vibration source to cause the soft tissue to vibrate. Further, an analog circuit capable of outputting high voltage, such as a high-voltage excitation module, and an ultrasonic transducer adapted to be excited by the high voltage to generate an ultrasound signal are utilized to emit the ultrasound signal to the soft tissue. Then, additional circuits and modules, such as an analog-to-digital converter with a high sampling frequency, a programmable counter and an elasticity analyzing module, are used to detect, sample and analyze an ultrasound echo signal resulting from reflection of the ultrasound signal by the soft tissue which is caused to vibrate by the external vibration source. As a result, the conventional ultrasonic measuring system including the abovementioned circuits and modules occupies a relatively large room and is usually relatively expensive.

SUMMARY

Therefore, an object of the disclosure is to provide a measuring apparatus and system for measuring elasticity of a biological tissue capable of alleviating the drawback of the conventional ultrasonic measuring system.

According to an aspect of the disclosure, a measuring system for measuring elasticity of a biological tissue is provided. The measuring system includes a mobile device and a measuring apparatus. The mobile device is configured to produce vibrations. The measuring apparatus includes a vibration conducting seat and an elasticity measuring device. The vibration conducting seat has an accommodation space for detachable mounting of the mobile device therein, and is adapted to abut against the biological tissue for conducting the vibrations produced by the mobile device to the biological tissue to cause the biological tissue to vibrate. The elasticity measuring device is mounted to the vibration conducting seat, is adapted to abut against the biological tissue along with the vibration conducting seat and includes an ultrasonic transducer and an elasticity analyzer. The ultrasonic transducer is operable to generate an ultrasound signal, to emit the ultrasound signal to the biological tissue, and to detect an ultrasound echo signal that results from reflection of the ultrasound signal by the biological tissue which is vibrating. The elasticity analyzer is configured to analyze the ultrasound echo signal to obtain an elasticity data of the biological tissue indicating an elasticity of the biological tissue.

According to another aspect of the disclosure, a measuring apparatus for measuring elasticity of a biological tissue adapted to be used with a mobile device capable of producing vibrations is provided. The measuring apparatus includes a vibration conducting seat and an elasticity measuring device. The vibration conducting seat has an accommodation space adapted for receiving the mobile device therein and is adapted to abut against the biological tissue for conducting the vibrations produced by the mobile device to the biological tissue to cause the biological tissue to vibrate. The elasticity measuring device is mounted to the vibration conducting seat, is adapted to abut against the biological tissue along with the vibration conducting seat, and includes an ultrasonic transducer and an elasticity analyzer. The ultrasonic transducer is operable to generate an ultrasound signal, to emit the ultrasound signal to the biological tissue, and to detect an ultrasound echo signal that results from reflection of the ultrasound signal by the biological tissue which is vibrating. The elasticity analyzer is configured to analyze the ultrasound echo signal to obtain an elasticity data of the biological tissue indicating an elasticity of the biological tissue.

BRIEF DESCRIPTION OF THE DRAWINGS

Other features and advantages of the disclosure will become apparent in the following detailed description of the embodiments with reference to the accompanying drawings, of which.

DETAILED DESCRIPTION

Figure 1:
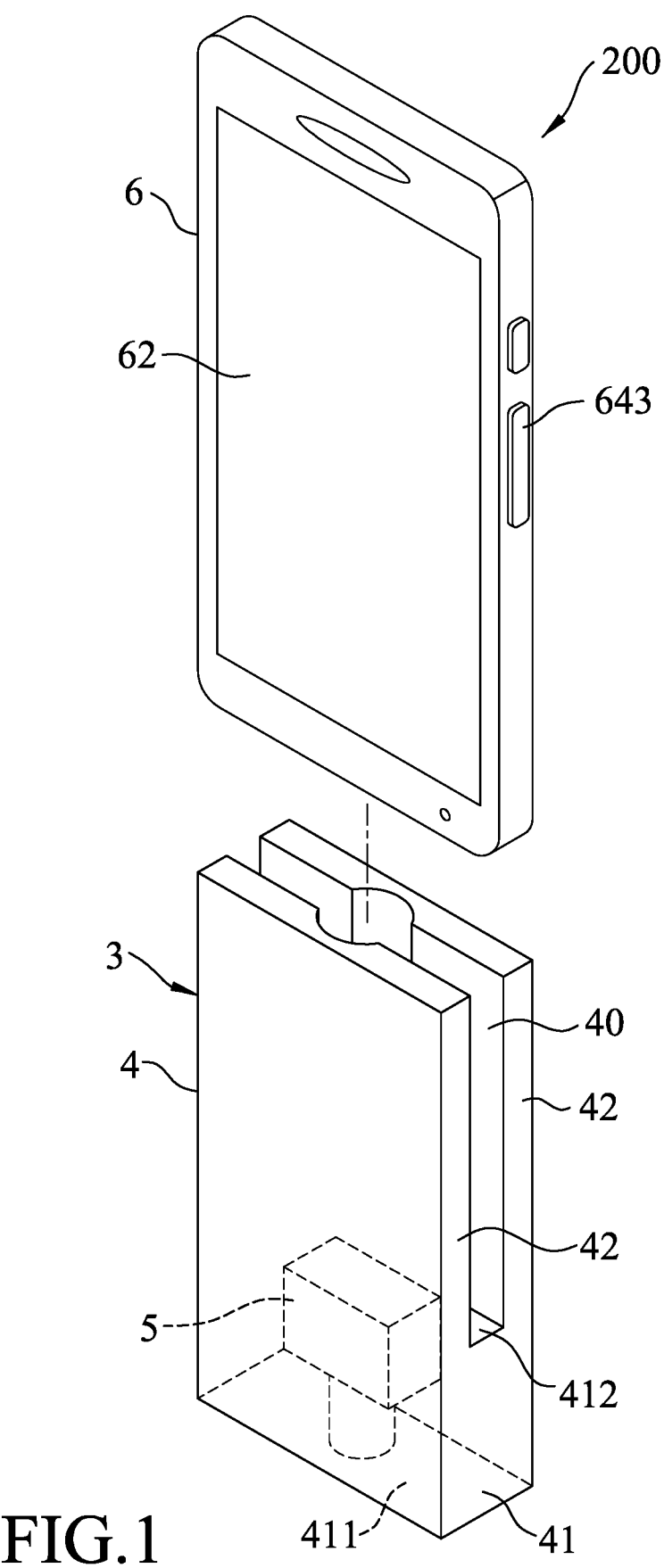
FIG. 1 is a partly exploded perspective view of a measuring system for measuring elasticity of a biological tissue according to a first embodiment of the present disclosure.
Figure 2:
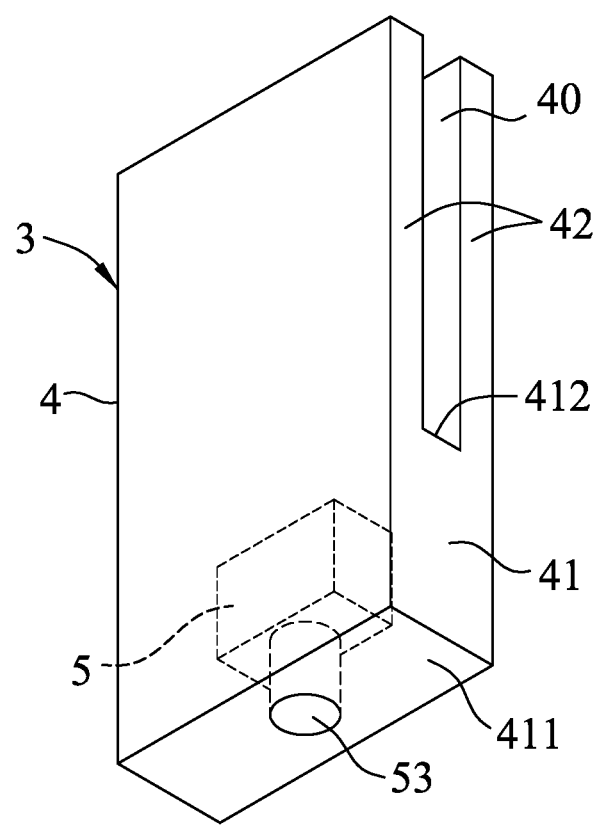
FIG. 2 is a schematic perspective view of an elasticity measuring device and a vibration conducting seat of the measuring system of the embodiment.
Figure 3:
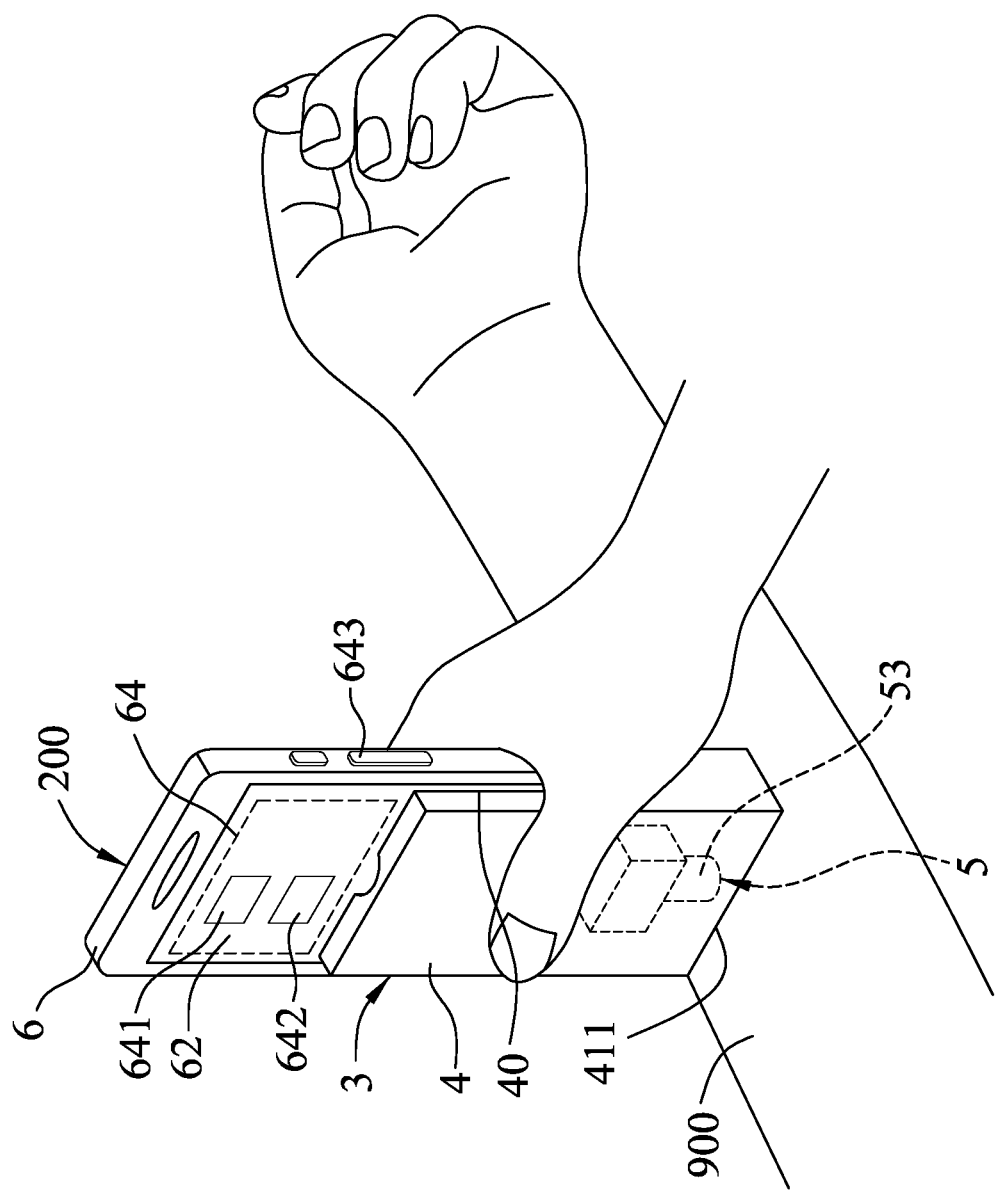
FIG. 3 is a schematic perspective view of the measuring system of the embodiment abutting against a biological tissue to be measured.

Referring to FIGS. 1 to 3, a measuring system 200 for measuring elasticity of a biological tissue according to an embodiment of this disclosure is shown. The measuring system 200 is adapted to abut against a surface of a biological tissue 900 to be measured, for example, to abut against a muscle tissue of a human body to measure an elasticity of the muscle tissue. The measuring system 200 includes a mobile device 6 and a measuring apparatus 3. The mobile device 6 is configured to produce vibrations and is detachably mounted to the measuring apparatus 3. The measuring apparatus 3 includes a vibration conducting seat 4 and an elasticity measuring device 5.

The vibration conducting seat 4 includes an abutment portion 41 and two wall portions 42. The abutment portion 41 has a first side 411 and a second side 412 opposite to the first side 411. The first side 411 of the abutment portion 41 is adapted to abut against the biological tissue 900 to enable the vibration conducting seat 4 to conduct the vibrations produced by the mobile device 6 to the biological tissue 900 to cause the biological tissue 900 to vibrate. The wall portions 42 extend from the second side 412 of the abutment portion 41, are spaced apart from each other, and cooperate with the abutment portion 41 to define an accommodation space 40 for receiving the mobile device 6 therein. Specifically, the wall portions 42 sandwich the mobile device 6 therebetween and the mobile device 6 abuts against the abutment portion 41 on the second side 412 so as to be positioned in the accommodating space 40. In this embodiment, the vibration conducting seat 4 is made of carbon fiber but the material for making the vibration conducting seat 4 is not limited to the example described herein.

Figure 4:
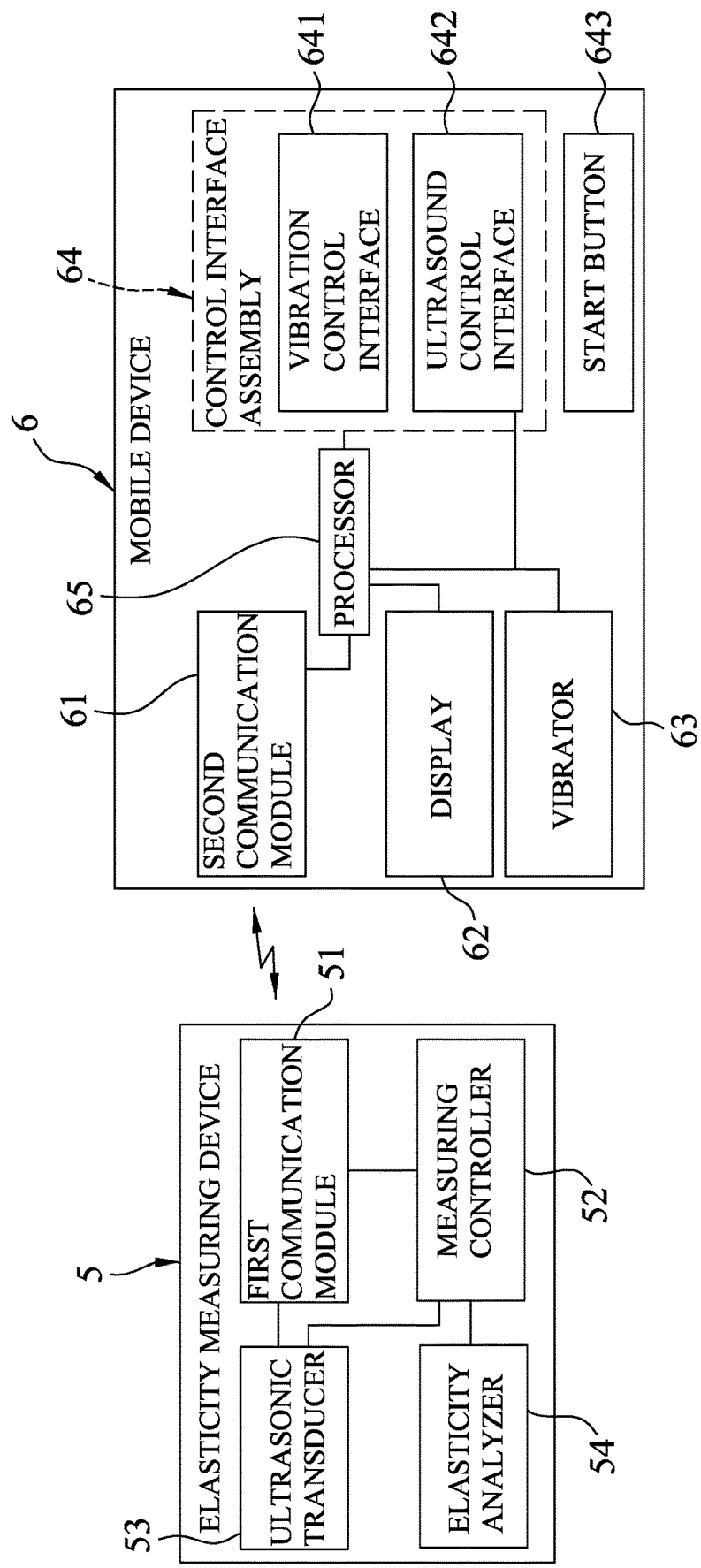
FIG. 4 is a schematic block diagram of the elasticity measuring device and a mobile device of the measuring system according to the embodiment.

The elasticity measuring device 5 is mounted to the vibration conducting seat 4 and is adapted to abut against the biological tissue 900 along with the vibration conducting seat 4. Further referring to FIG. 4, the elasticity measuring device 5 includes a first communication module 51, a measuring controller 52, an ultrasonic transducer 53, and an elasticity analyzer 54.

The first communication module 51 is configured to communicate with the mobile device 6 to receive a control signal from the mobile device 6. The measuring controller 52 is communicatively connected to the first communication module 51, the ultrasonic transducer 53, and the elasticity analyzer 54, and is configured to, in response to receipt of the control signal from the first communication module 51, control operation of the ultrasonic transducer 53 and the elasticity analyzer 54.

The ultrasonic vibration transducer 53 is flush with a surface of the first side 411 of the abutment portion 41, and is exposed to an external environment. When the vibration conducting seat 4 is abutted against the biological tissue 900, the ultrasonic vibration transducer 53 is also brought to abut against the biological tissue 900. The ultrasonic transducer 53 is operable to generate an ultrasound signal, to emit the ultrasound signal with an excitation frequency to the biological tissue 900, and to detect an ultrasound echo signal that results from reflection of the ultrasound signal by the biological tissue 900 which is vibrating because of the vibrations produced by the mobile device 6 and conducted by the vibration conducting seat 4.

The elasticity analyzer 54 is configured to be controlled to sample the ultrasound echo signal according to a sampling frequency, and to analyze the ultrasound echo signal thus sampled to obtain an elasticity data of the biological tissue 900 indicating an elasticity of the biological tissue 900. Since how the ultrasonic transducer 53 generate the ultrasound signal and detect the ultrasound echo signal, and how the elasticity analyzer 54 sample and analyze the ultrasound echo signal to obtain the elasticity data of the biological tissue 900 is well known in the pertinent art, further details of the same are omitted for the sake of brevity.

The mobile device 6 is, for example, but not limited to, a smart phone, a tablet PC or a personal digital assistant (PDA). The mobile device 6 includes a second communication module 61, a display 62, a vibrator 63, and a processor 65. The second communication module 61 is communicatively connected to the first communication module 51 for transmitting the control signal to the measuring controller 52 and receiving the elasticity data from the elasticity analyzer 54. Specifically, each of the first communication module 51 and the second communication module 61 includes one of a wired transceiver, a wireless transceiver and a combination thereof for communications with each other. In this embodiment, the first communication module 51 and the second communication module 61 communicates wirelessly using, for example, but not limited to, Bluetooth® communication protocol.

The vibrator 63 is operable to produce the vibrations. The processor 65 is communicatively connected to the second communication module 61, the display 62 and the vibrator 63, and is operable to control the vibrator 63 to produce the vibrations, and operable to control the display 62 to display the elasticity data of the biological tissue 900 received by the second communication module 61.

Specifically, the processor 65 is configured to control the display 62 to display a control interface assembly 64 including a vibration control interface 641 and an ultrasound control interface 642. The vibration control interface 641 allows user operation thereon to set one of a vibration frequency, a vibration time duration and a combination thereof (e.g., to assign a value of the vibration frequency and/or to assign a value of the vibration time duration).

The processor 65 is configured to, in response to the user operation on the vibration control interface 641, control the vibrator 63 to produce the vibrations which have the vibration frequency when the vibration frequency is set via the vibration control interface 641 and which last for the vibration time duration when the vibration time duration is set via the vibration control interface 641.

It should be noted that in one embodiment, the mobile device 6 may store in advance a preset frequency value for the vibration frequency and a preset duration value for the vibration time duration. The processor 65 is further configured to, in response to the user operation on the vibration control interface 641, control the vibrator 63 to produce the vibrations which have the vibration frequency at the preset frequency value when the vibration frequency is not set (e.g., not assigned with a value) via the vibration control interface 641 and which last for the predetermined vibration time duration at the preset duration value when the vibration time duration is not set (e.g., not assigned with a value) via the vibration control interface 641.

The ultrasound control interface 642 displayed on the display 62 also allows user operation thereon to set one of an excitation frequency, a sampling frequency and a combination thereof (e.g., to assign a value of the excitation frequency and/or to assign a value of the sampling frequency). The processor 65 is further configured to, in response to the user operation on the ultrasound control interface 642, generate the control signal that contains information of one of the excitation frequency, the sampling frequency and the combination thereof, and that is to be transmitted by the second communication module 61.

After generation of the control signal by the processor 65, the second communication module 61 is configured to transmit the control signal to the first communication module 51. The measuring controller 52 is triggered by the control signal received by the first communication module 51 to control the ultrasonic transducer 53 to generate the ultrasound signal according to the excitation frequency when the excitation frequency is set via the ultrasound control interface 642, to emit the ultrasound signal to the biological tissue 900, and to detect the ultrasound echo signal that results from reflection of the ultrasound signal by the biological tissue 900 which is vibrating. The control signal further triggers the measuring controller 52, when the sampling frequency is set via the ultrasound control interface 642, to control the elasticity analyzer 54 to sample the ultrasound echo signal according to the sampling frequency, and analyze the ultrasound echo signal thus sampled to obtain the elasticity data.

Note that in one embodiment of the present disclosure, the mobile device 6 may store in advance a preset excitation value for the excitation frequency and a preset sampling value for the sampling frequency. The processor 65 is configured to, in response to the user operation on the ultrasound control interface 642, generate the control signal that contains information of the excitation frequency having the preset excitation value when the excitation frequency is not set (e.g., not assigned with a value) via the ultrasound control interface 642 and that contains information of the sampling frequency having the preset sampling value when the sampling frequency is not set (e.g., not assigned with a value) via the ultrasound control interface 642 In this way, the control signal triggers the measuring controller 52 to control the ultrasonic transducer 53 to generate the ultrasound signal according to the excitation frequency at the preset excitation value when the excitation frequency is not assigned with a value via the ultrasound control interface 642. The control signal further triggers the controller 52 to, when the sampling frequency is not assigned with a value via the ultrasound control interface 642, control the elasticity analyzer 54 to sample the ultrasound echo signal according to the predetermined sampling frequency at the preset sampling value, and analyze the ultrasound echo signal thus sampled to obtain the elasticity data.

In this embodiment, the mobile device 6 further includes a start button 643. The processor 65 is configured to, when the start button 643 is operated, control the vibrator 63 to start to produce the vibrations, and control the second communication module 61 to transmit the control signal to the first communication module 51 of the elasticity measuring device 5. The start button 643 may be any one of physical buttons of the mobile device 6, for example, a volume adjustment button of the mobile device 6.

Note that in other embodiments, the start button may be a virtual button which is displayed on the display 62 when the display 62 is controlled by the processor 65 to display the same and which allows user operation thereon.

The term "processor" and "controller" may refer to any device or portion of a device that processes electronic data from registers and/or memory to transform that electronic data into other electronic data. For example, each of the measuring controller 52 and the processor 65 is, but not limited to, a single core processor, a multi-core processor, a dual-core mobile processor, a microprocessor, a microcontroller, a digital signal processor (DSP), a field-programmable gate array (FPGA), an application specific integrated circuit (ASIC), a radio-frequency integrated circuit (RFIC), etc. The elasticity analyzer 54 may include, but not limited to, one of an analog-to-digital converter operable at a high sampling frequency, a programmable counter, a digital signal processor, and any combination thereof that is able to carry out the sampling and analyzing functions of the disclosure. For example, a FibroScan® device can be used as the elasticity analyzer 54.

Note that any mobile device capable of producing vibrations can serve as the mobile device 6 of the measuring system 200 of the present disclosure to provide a vibration source to vibrate a biological tissue to be measured. Before utilizing the mobile device, an application program (App) may be downloaded to be executed by a processor of the mobile device to provide the control interface assembly 64.

To measure an elasticity of a muscle tissue of a human body, for example, a muscle tissue of an arm, the control interface assembly 64 displayed on the mobile device 6 is first operated by the user to set the vibration frequency and the vibration time duration via the vibration control interface 641, and to set the excitation frequency and the sampling frequency via the ultrasound control interface 642. Then, the mobile device 6 is inserted into the accommodation space 40 of the vibration conducting seat 4.

The first side 411 of the abutment portion 41 of the vibration conducting seat 4 is brought to abut against the biological tissue 900 to be measured, i.e., the muscle tissue of the arm, along with the ultrasonic vibration transducer 53.

Then, the start button 643 is operated to enable the processor 65 to control the vibrator 63 to start to produce the vibrations which have the vibration frequency, and which last for the vibration time duration. As a result, the vibrations produced by the vibrator 63 is conducted by the vibration conducting seat 4 to the biological tissue 900 to cause the biological tissue 900 to vibrate. That is, the muscle tissue of the arm is vibrated by the mobile device 6 via the vibration conducting seat 4.

As the start button 643 is operated, the processor 65 is enabled to also control the second communication module 61 to transmit the control signal to the first communication module 51 of the elasticity measuring device 5. The measuring controller 52 is triggered by the control signal to control the ultrasonic transducer 53 to generate the ultrasound signal according to the excitation frequency, to emit the ultrasound signal, and to detect the ultrasound echo signal that results from reflection of the ultrasound signal by the biological tissue 900 which is vibrating because of the vibrations produced by the mobile device 6. The measuring controller 52 is further triggered by the control signal to control the elasticity analyzer 54 to sample the ultrasound echo signal according to the sampling frequency, and analyze the ultrasound echo signal thus sampled to obtain the elasticity data. The first communication module 51 then transmits the elasticity data from the elasticity analyzer 54 to the second communication module 61 of the mobile device 6, and the processor 65 controls the display 62 to display the elasticity data of the biological tissue 900.

In this embodiment, the wall portions 42 of the vibration conducting seat 4 are provided to sandwich the mobile device 6 therebetween but the present disclosure is not limited to this example. That is to say, the mechanism of the vibration conducting seat 4 for mounting of the mobile device 6 can be modified to have a different structure as long as the vibrations produced by the mobile device 6 can be conducted to the biological tissue 900 via the vibration conducting seat 4 that is abutted by the mobile device 6.

To sum up, by virtue of the cooperation among the vibration conducting seat 4, the elasticity measuring device 5 and the mobile device 6 that is readily available and that serves as a source of vibration, the biological tissue 900 to be measured can be vibrated by the mobile device 6 with the aid of the vibration conducting seat 4. Then, the elasticity data of the biological tissue 900 can be obtained by controlling the elasticity measuring device 5 to emit an ultrasound signal, to detect an ultrasound echo signal, and to sample and analyze the ultrasound echo signal. In this way, a relatively compact measuring system for measuring elasticity of a biological tissue is provided.

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A measuring apparatus for measuring elasticity of a biological tissue adapted to be used with a mobile device capable of producing vibrations, the measuring apparatus comprising:
   a vibration conducting seat which has an accommodation space adapted for receiving the mobile device therein, which includes two wall portions spaced apart from each other and adapted to sandwich the mobile device therebetween, and which is adapted to abut against the biological tissue for conducting the vibrations produced by the mobile device to the biological tissue to cause the biological tissue to vibrate; and
   an elasticity measuring device mounted to said vibration conducting seat, adapted to abut against the biological tissue along with said vibration conducting seat, and including
   an ultrasonic transducer operable to generate an ultrasound signal, to emit the ultrasound signal to the biological tissue, and to detect an ultrasound echo signal that results from reflection of the ultrasound signal by the biological tissue which is vibrating, and
   an elasticity analyzer configured to analyze the ultrasound echo signal to obtain an elasticity data of the biological tissue indicating an elasticity of the biological tissue.

2. The measuring apparatus as claimed in claim 1, wherein said elasticity measuring device further includes a first communication module adapted to communicate with the mobile device to receive a control signal from the mobile device, and a measuring controller communicatively connected to said first communication module, said ultrasonic transducer, and said elasticity analyzer, and configured to, in response to receipt of the control signal from said first communication module,
   control said ultrasonic transducer to generate the ultrasound signal according to the control signal and to detect the ultrasound echo signal, and
   control said first communication module to transmit the elasticity data to the mobile device.

3. The measuring apparatus as claimed in claim 2, wherein said measuring controller is configured to, in response to receipt of the control signal by said first communication module, further control said elasticity analyzer to sample the ultrasound echo signal according to the control signal and to analyze the ultrasound echo signal thus sampled to obtain the elasticity data to be transmitted to the mobile device via said first communication module.

4. The measuring apparatus as claimed in claim 2, wherein said first communication module includes one of a wired transceiver, a wireless transceiver and a combination thereof adapted to be communicatively connected to the mobile device for receiving the control signal from the mobile device and transmitting the elasticity data to the mobile device.

5. The measuring apparatus as claimed in claim 1, wherein said vibration conducting seat further includes an abutment portion having a first side adapted to abut against the biological tissue to enable the vibration conducting seat to conduct the vibrations produced by the mobile device to the biological tissue, said two wall portions extending from a second side of said abutment portion and cooperating with said abutment portion to define said accommodation space, said abutment potion adapted to be abutted by the mobile device on the second side so as to position the mobile device in the accommodating space, said ultrasonic transducer being flush with a surface of the first side of said abutment portion to abut against the biological.

6. A measuring system for measuring elasticity of a biological tissue, comprising:
   a mobile device configured to produce vibrations; and
   a measuring apparatus including a
   a vibration conducting seat which has an accommodation space for detachable mounting of said mobile device therein, which includes two wall portions spaced apart from each other and sandwiching said mobile device therebetween, and which is adapted to abut against the biological tissue for conducting the vibrations produced by said mobile device to the biological tissue to cause the biological tissue to vibrate; and
   an elasticity measuring device mounted to said vibration conducting seat, adapted to abut against the biological tissue along with said vibration conducting seat, and including
   an ultrasonic transducer operable to generate an ultrasound signal, to emit the ultrasound signal to the biological tissue, and to detect an ultrasound echo signal that results from reflection of the ultrasound signal by the biological tissue which is vibrating, and
   an elasticity analyzer configured to analyze the ultrasound echo signal to obtain an elasticity data of the biological tissue indicating an elasticity of the biological tissue.

7. The measuring system as claimed in claim 6, wherein said elasticity measuring device further includes a first communication module configured to communicate with said mobile device to receive a control signal from said mobile device, and a measuring controller communicatively connected to said first communication module, said ultrasonic transducer, and said elasticity analyzer, and configured to, in response to receipt of the control signal from said first communication module, control operation of said ultrasonic transducer, said mobile device including
   a second communication module communicatively connected to said first communication module for transmitting the control signal to said measuring controller and receiving the elasticity data from said elasticity analyzer,
   a vibrator operable to produce the vibrations,
   a display, and
   a processor communicatively connected to said second communication module, said display and said vibrator, and operable to control said vibrator to produce the vibrations, and operable to control said display to display the elasticity data of the biological tissue received by said second communication module.

8. The measuring system as claimed in claim 7, wherein said processor is configured to:
   control said display to display a vibration control interface allowing user operation thereon to set one of a vibration frequency, a vibration time duration and a combination thereof; and
   in response to the user operation on the vibration control interface, control said vibrator to produce the vibrations which have the vibration frequency when the vibration frequency is set via said vibration control interface and which last for the vibration time duration when the vibration time duration is set via said vibration control interface.

9. The measuring system as claimed in claim 8, wherein said mobile device further includes a start button, and
said processor is configured to, when the start button is operated, control said vibrator to start to produce the vibrations, and control said second communication module to transmit the control signal to said first communication module of said elasticity measuring device.

10. The measuring system as claimed in claim 7, wherein:
said processor is further configured to
control said display to display an ultrasound control interface allowing user operation thereon to set one of an excitation frequency, a sampling frequency and a combination thereof, and
in response to the user operation on the ultrasound control interface, generate the control signal that contains information of the one of the excitation frequency, the sampling frequency and the combination thereof, and that is to be transmitted by said second communication module; and
after generation of the control signal, said second communication module is configured to transmit the control signal to said first communication module, the control signal triggering said measuring controller to control said ultrasonic transducer to generate the ultrasound signal according to the excitation frequency when the excitation frequency is set via said ultrasound control interface, and to, when the sampling frequency is set via said ultrasound control interface, control said elasticity analyzer to sample the ultrasound echo signal according to the sampling frequency, and analyze the ultrasound echo signal thus sampled to obtain the elasticity data.

11. The measuring system as claimed in claim 10, wherein said processor is further configured to:
control said display to display a vibration control interface allowing user operation thereon to set one of a vibration frequency, a vibration time duration and a combination thereof; and
in response to the user operation on the vibration control interface, control said vibrator to produce the vibrations which have the vibration frequency when the vibration frequency is set via said vibration control interface and which last for the vibration time duration when the vibration time duration is set via said vibration control interface.

12. The measuring system as claimed in claim 11, wherein said mobile device further includes a start button, and
said processor is configured to, when the start button is operated, control said vibrator to start to produce the vibrations, and control said second communication module to transmit the control signal to said first communication module of said elasticity measuring device.

\* \* \* \* \*

UNITED STATES PATENT AND TRADEMARK OFFICE
CERTIFICATE OF CORRECTION

PATENT NO. : 11,213,277 B2
APPLICATION NO. : 16/706913
DATED : January 4, 2022
INVENTOR(S) : Huang et al.

Page 1 of 1

It is certified that error appears in the above-identified patent and that said Letters Patent is hereby corrected as shown below:

In the Claims

Column 8, Claim 5, Line 9:
After "biological" insert -- tissue --

Signed and Sealed this
Twenty-first Day of June, 2022

Katherine Kelly Vidal
Director of the United States Patent and Trademark Office